(12) United States Patent
Ali et al.

(10) Patent No.: US 9,023,382 B2
(45) Date of Patent: May 5, 2015

(54) MEDICAMENT CARRIER COMPOSITION AND METHOD OF FORMING A FILM THEREFROM

(75) Inventors: Shaukat Ali, Monmouth Junction, NJ (US); Anisul Quadir, Hackettstown, NJ (US)

(73) Assignee: BASF Corporation, Florham Park, NJ (US)

(*) Notice: Subject to any disclaimer, the term of this patent is extended or adjusted under 35 U.S.C. 154(b) by 1647 days.

(21) Appl. No.: 11/916,733

(22) PCT Filed: Apr. 24, 2006

(86) PCT No.: PCT/US2006/015236
§ 371 (c)(1),
(2), (4) Date: Jul. 10, 2008

(87) PCT Pub. No.: WO2006/135491
PCT Pub. Date: Dec. 21, 2006

(65) Prior Publication Data
US 2009/0053285 A1 Feb. 26, 2009

Related U.S. Application Data

(60) Provisional application No. 60/688,536, filed on Jun. 8, 2005.

(51) Int. Cl.
*A61K 9/70* (2006.01)
*A61K 31/79* (2006.01)
(Continued)

(52) U.S. Cl.
CPC .............. *A61K 31/192* (2013.01); *A61K 9/7007* (2013.01); *A61K 9/7015* (2013.01); *A61K 9/7053* (2013.01); *A61K 31/135* (2013.01)

(58) Field of Classification Search
CPC . A61K 8/8176; A61K 8/8182; A61K 9/0056; A61K 9/006; A61K 9/7007; A61K 9/7075; A61K 9/7053
See application file for complete search history.

(56) References Cited

U.S. PATENT DOCUMENTS 3,957,966 A * 5/1976 Valan ........................... 424/482
4,517,173 A   5/1985 Kizawa et al.
(Continued)

FOREIGN PATENT DOCUMENTS

GB    2078771 A   1/1982
WO    WO 01/54674 A1   8/2001

OTHER PUBLICATIONS

Buhler, "Kollidon, Polyvinylpyrrolidone for the pharmaceuticla industry", BASF Aktiengesellschaft, No. 6, 2002. pp. 40-41, 73, 75-76, 107-111, 114, 118-120, 122, 196-197, 251-254.
(Continued)

*Primary Examiner* — Lakshmi Channavajjala
(74) *Attorney, Agent, or Firm* — Howard & Howard Attorneys PLLC (57) ABSTRACT

A medicament carrier composition includes a medicament and a polymer component including a polyvinylpyrrolidone having a weight average molecular weight of at least 700,000 g/mol. The medicament carrier composition has a viscosity of from 500 to 5,000 cps at 250 C, is substantially free of cellulose, and includes an auxiliary polymer. The medicament carrier composition is used to form a film that is also substantially free of cellulose. The film has a consistent thickness and size, and an increased flexibility and increased moisture resistance due to the polyvinylpyrrolidone. The medicament carrier composition is also used in a method of forming the film. The method includes the steps of providing the medicament and the polymer component. The method also includes the step of combining the polymer component and the medicament to form the medicament carrier composition. The method further includes the step of drying the medicament carrier composition to form the film.

23 Claims, 6 Drawing Sheets

(51) Int. Cl.
*A61K 31/192* (2006.01)
*A61K 31/135* (2006.01)

(56) References Cited

U.S. PATENT DOCUMENTS

| | | | |
|---|---|---|---|
| 5,047,244 | A | 9/1991 | Sanvordeker et al. |
| 5,156,601 | A * | 10/1992 | Lorenz et al. ............... 604/307 |
| 5,489,436 | A | 2/1996 | Hoy et al. |
| 5,700,478 | A * | 12/1997 | Biegajski et al. ............ 424/434 |
| 5,948,430 | A | 9/1999 | Zerbe et al. |
| D423,302 | S | 4/2000 | Haner et al. |
| 6,159,498 | A | 12/2000 | Tapolsky et al. |
| 6,294,045 | B1 * | 9/2001 | Hidaka et al. ................ 156/327 |
| 6,306,372 | B1 | 10/2001 | Stier et al. |
| 6,432,415 | B1 | 8/2002 | Osborne et al. |
| 6,472,000 | B1 | 10/2002 | Gudas et al. |
| 6,562,363 | B1 | 5/2003 | Mantelle et al. |
| 6,585,997 | B2 | 7/2003 | Moro et al. |
| 6,596,298 | B2 | 7/2003 | Leung et al. |
| 6,620,428 | B1 | 9/2003 | Hoeck et al. |
| 6,669,957 | B1 | 12/2003 | Laruelle et al. |
| 6,709,671 | B2 | 3/2004 | Zerbe et al. |
| 6,709,713 | B2 | 3/2004 | Augello et al. |
| 6,723,342 | B1 | 4/2004 | Augello et al. |
| 6,726,054 | B2 | 4/2004 | Fagen et al. |
| 6,767,557 | B2 | 7/2004 | Ulrich et al. |
| 6,806,256 | B2 | 10/2004 | Ulrich et al. |
| 6,923,981 | B2 | 8/2005 | Leung et al. |
| 2002/0014307 | A1 | 2/2002 | Hidaka et al. |
| 2004/0156794 | A1 | 8/2004 | Barkalow et al. |
| 2004/0224007 | A1 | 11/2004 | Zhang |
| 2005/0008735 | A1 | 1/2005 | Pearce |
| 2005/0136096 | A1 | 6/2005 | Davidson |
| 2005/0226823 | A1 | 10/2005 | Krumme et al. |
| 2006/0002989 | A1 | 1/2006 | Ahmed et al. |
| 2006/0039953 | A1 | 2/2006 | Leung et al. |

OTHER PUBLICATIONS

Ali et al., High Molecular Weight Povidone Polymer Based Films for Fast Dissolving Drug Delivery Applications:, BASF Corporation, Pharma Solutions, Presentation, Nov. 2005, Poster T2168, pp. 1-12.

Ali et al., "BASF Polymers in Film Development Technology for Drug Delivery Applications", BASF Corporatioin, Pharma Solutions, Presentation, Jun. 2005, Poster #501, pp. 1-12.

Lindgren et al. "Prevalence of Swallowing Complaints and Clinical Findings . . . ", Dysphagia, No. 6, 1991, pp. 187-192.

Doheny, "You Really Expect Me to Swallow Those Horse Pills", American Druggist, 1993, pp. 34-35, 39.

Slawson et al. "What to Do When Patients Can't Swallow Their Medications", Pharmacy Times, 1985, pp. 90-96.

Rama Roa et al. "Drug Diffusion from Cellulose Acetate-Polyvinyl Pyrrolldone Free Films . . . ", Indian Journal of Pharm. Sci., 1996, pp. 246-250.

Cilurzo et al. "Polymethacrylates as crystallization inhibitors in monolayer . . . ", EJPB, No. 60, 2005, pp. 61-66.

Ananay Gonzalez Novoa et al. "Physical solid-state properties and dissolution of sustained-release . . . ", EJPB, No. 59, 2004, pp. 343-350.

Nafee et al. "Design and characterization of mucoadhesive buccal patches . . . ", Acta Pharm. No. 53, 2003, pp. 199-212.

Baumgartner et al. "Network Structure of Cellulose Ethers Used in Pharmaceutical . . . ", Pharmaceutical Research, vol. 19, No. 8, 2002, pp. 1084-1090.

Borsadia et al. "Quick-Dissolving Films—A Novel Approach to Drug Delivery", Drug Delivery, vol. 3, No. 3, 2003, pp. 1-7.

Stier, "Masking Bitter Taste of Pharmaceutical Actives", Drug Delivery Technology, vol. 4, No. 2, 2004, pp. 53-57.

Schmidt, "Killidon (Polyvinylpyrrolidone), A Review on its Use in Granulation", BASF ExAct, No. 2, 1999, pp. 5-13.

Iordanskii et al., Research Paper: "Modeling of the drug delivery from a hydrophilic transdermal therapeutic system across polymer membrane", European Journal of Pharmaceutics and Biopharmaceutics, 49 (2000) pp. 287-293.

Lee et al., "Oral mucosa controlled delivery of LHRH by bilayer mucoadhesive polymer systems", Journal of Controlled Release, 37 (1995) pp. 251-261.

Solomonidou et al., "Effect of carbomer concentration and degree of neutralization on the mucoadhesivee properties of polymer films", J. Biomater. Sci. Polymer Edn, vol. 12, No. 11 (2001) pp. 1191-1205.

Supplementary European Search Report for Application No. EP 06 75 1070 completed on Jun. 13, 2012, 3 pages.

* cited by examiner

MEDICAMENT CARRIER COMPOSITION AND METHOD OF FORMING A FILM THEREFROM

CROSS REFERENCE TO RELATED APPLICATION

This application claims priority to and all the advantages of International Patent Application No. PCT/US2006/015236, filed on Apr. 24, 2006, which claims priority to U.S. provisional patent application Ser. No. 60/688,536, which was filed on Jun. 8, 2005.

FIELD OF THE INVENTION

The present invention generally relates to medicament carrier composition and a method of forming a film. More specifically, the medicament carrier composition is used to form a film and the medicament carrier composition includes a medicament and a polymer component including a polyvinylpyrrolidone having a weight average molecular weight of at least 700,000 g/mol.

DESCRIPTION OF THE RELATED ART

Medicament carrier compositions and films including polymers, such as polyvinylpyrrolidones, are well known in the art. Specifically, the compositions and the films are known to be used in both pharmaceutical and cosmetic applications. Typically, the compositions are formed by dissolving the polymers in a solvent. The films are then formed by drying the compositions in an oven to evaporate the solvent.

Many of the polymers that are known to be used in the compositions and films have low weight average molecular weights of less than 150,000 g/mol. The low weight average molecular weights contribute to difficulties in forming the films and cause the compositions to have low viscosities. The compositions having the low viscosities tend to form films of uneven thicknesses and sizes that do not adequately adhere to backing layers, thereby forming defective films requiring alteration of sizes and shapes of the films and recycling of the films for re-processing. This results in decreased production efficiency and increased production costs.

Specific compositions including polyvinylpyrrolidone as the polymer are disclosed in U.S. Pat. No. 6,585,997 to Moro et al. The compositions disclosed in the Examples of the '997 patent, specifically in Examples 3 and 4, include mixtures including polyvinylpyrrolidone having a molecular weight of 1,000,000 g/mol, cellulose, and acrylate polymers. These compositions are utilized in multi-layer films that include medicaments. However, these compositions themselves do not include the medicaments and are not utilized in monolayer films. Additionally, inclusion of cellulose in these mixtures contributes to rigidity of the film, i.e., decreased flexibility. Also, the cellulose is sensitive to moisture and has a tendency to decompose when exposed to moisture. By using these compositions to form the multi-layered films of the '997 patent, productions costs are increased, as additional steps are required. As such, the compositions and the multi-layered films disclosed in the '997 patent are not optimized for commercial use and are expensive to produce.

Accordingly, there remains an opportunity to form a medicament carrier composition and a film including a medicament and a polymer component including a polyvinylpyrrolidone having a particular weight average molecular weight. There also remains an opportunity to form a film that is not defective, does not require alteration of size and shape, and does not require recycling for re-processing. This increases production efficiency and decreases production costs. There further remains an opportunity to form a film having increased flexibility and increased moisture resistance.

SUMMARY OF THE INVENTION AND ADVANTAGES

The present invention provides a medicament carrier composition including a medicament and a polymer component including a polyvinylpyrrolidone having a weight average molecular weight of at least 700,000 g/mol. The medicament carrier composition has a viscosity of from 500 to 5,000 cps at 25° C. The present invention also provides a method of forming a film from the medicament carrier composition. The method includes the steps of providing the medicament and providing the polymer component. The method also includes the step of combining the polymer component and the medicament to form the medicament carrier composition having the viscosity of from 500 to 5,000 cps at 25° C. The method further includes the step of drying the medicament carrier composition to form the film.

The polymer component including the particular polyvinylpyrrolidone contributes to a viscosity of the medicament carrier composition such that the film has a consistent thickness and size. When the film has consistent thickness and size, the film is not defective and alteration of sizes and shapes of the film and recycling of the film for re-processing is not required. This increases production efficiency and decreases production costs. Further, the polymer component contributes to an increased flexibility and increased moisture resistance of the film.

BRIEF DESCRIPTION OF THE SEVERAL VIEWS OF THE DRAWINGS

Other advantages of the present invention will be readily appreciated, as the same becomes better understood by reference to the following detailed description when considered in connection with the accompanying drawings wherein.

DETAILED DESCRIPTION OF A PREFERRED EMBODIMENT

Figure 1A:
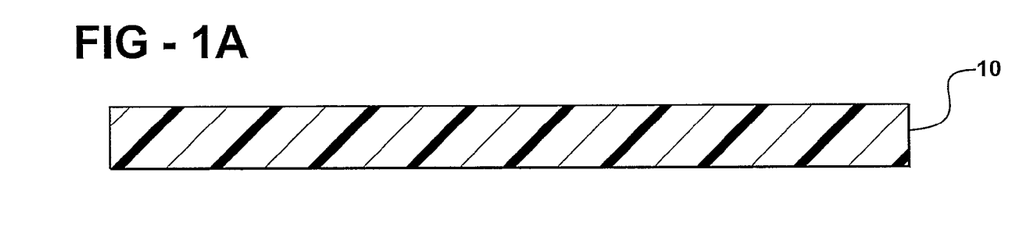
FIG. 1a is a side cross-sectional view of a first embodiment of the present invention wherein a film is a single layer (a monolayer)
Figure 1B:
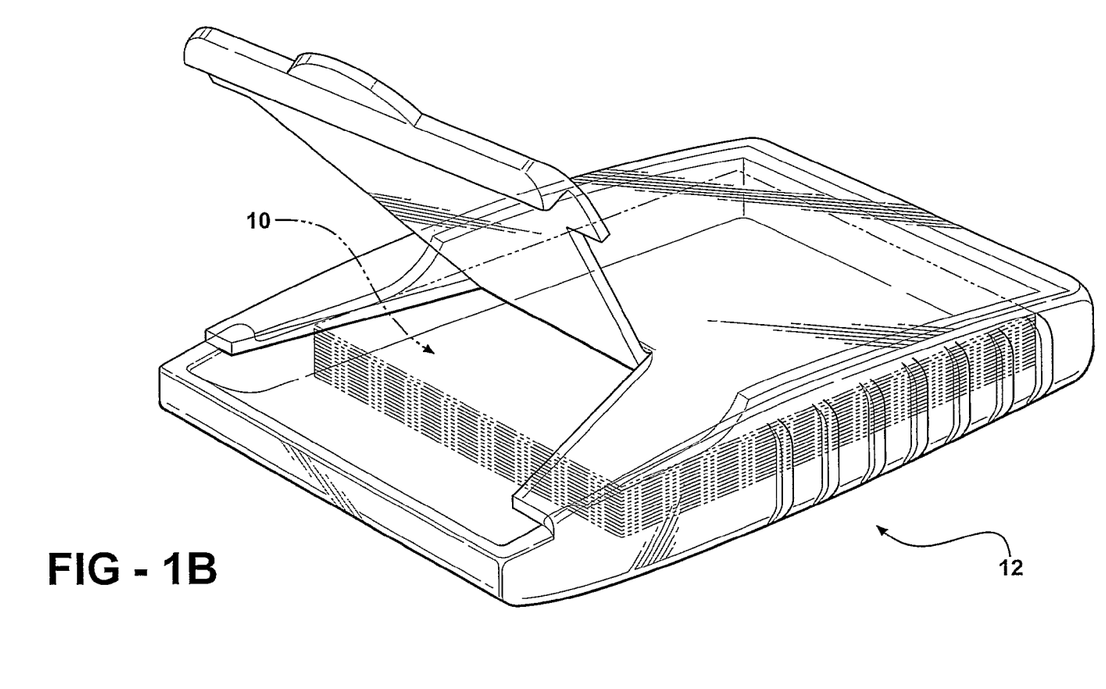
FIG. 1b is a perspective view of a film dispensed in an article.

The present invention provides a medicament carrier composition (composition) for use in a film (10) and a method of forming the film (10) from the medicament carrier composition. The present invention also preferably includes the film (10) formed from the medicament carrier composition, as shown in FIGS. 1a and 1b. Each of the composition and the film (10) include a medicament and a polymer component including a polyvinylpyrrolidone having a weight average molecular weight of at least 700,000 g/mol. The composition also has a viscosity of from 500 to 5,000 cps at 25° C. The polymer component, the film (10), and the method are each described in greater detail below.

The medicament may be any medicament known in the art. The terminology "medicament" includes not only any agent that promotes recovery from an injury or ailment, but also includes any agent that promotes health and/or cosmetic benefits. In one embodiment, the medicament is selected from the group of pharmaceuticals, nutrients, vitamins, minerals, cosmeceuticals, cosmetics, and combinations thereof. It is to be understood that the medicament may include a single pharmaceutical, nutrient, vitamin, mineral, cosmeceutical, cosmetic, and combinations thereof.

In another embodiment, the medicament includes the cosmeceuticals which may include, but are not limited to, a breath freshener. In still another embodiment, the medicament includes the vitamins which may include, but are not limited to, carotene (vitamin A), beta-carotene, thiamine (vitamin B1), riboflavin (vitamin B2), niacinimide ((vitamin B3), pantothenic acid (vitamin B5), pyridoxine (vitamin B6), choline (vitamin B7), inositol, biotin (vitamin B8), folic acid (vitamin B9), para-aminobenzoic acid (vitamin B10), cobalamin (vitamin B12), orotic acid (vitamin B13), pangamic acid (vitamin B15), laetrile (vitamin B17), ascorbic acid (vitamin C), vitamin P, calciforol (vitamin D), tocopherol (vitamin E), menadione (vitamin K), and combinations thereof.

In a further embodiment, the medicament includes the minerals which may include, but are not limited to, sodium, potassium, calcium, iron, iodine, magnesium, zinc, selenium, copper, manganese, chromium, molybdenum, and combinations thereof. In yet a further embodiment, the medicament includes the nutrients which may include, but are not limited to, fats, proteins, carbohydrates, and combinations thereof.

In another embodiment, the medicament includes the pharmaceuticals which may include, but are not limited to, hypnotics, sedatives, anti-epileptics, awakening agents, psychoneurotropic agents, neuromuscular blocking agents, antispasmodic agents, anti-histamines, anti-allergics, cardiotonics, anti-arrhythmics, diuretics, hypotensives, vasopressors, anti-tussive expectorants, hormones, anti-diabetics, anti-tumor agents, antibiotics, chemotherapeutics, narcotics, anti-anginal agents, anti-inflammatory analgesic agents, local anesthetics, bactericides, disinfectants, vasoconstrictors, hemostatics, antibiotics, keratolytics, cauterizing agents, anti-virals, and combinations thereof.

More specifically, examples of anti-allergics (e.g., antihistamines) include, but are not limited to, amlexanox, astemizole, azelastinep, emirolast, alopatadine, cromolyn, fenpiprane, repirinast, tranilast, traxanox, azithronmycin, fexofenadine, desloratadine, diphenhydramine, and combinations thereof. Also, non-limiting examples of anti-anginal agents include nifedipine, atenolol, bepridil, carazolol, and epanolol, and combinations thereof.

Additionally, examples of anti-inflammatory analgesic agents include, but are not limited to, acetaminophen, methyl salicylate, monoglycol salicylate, aspirin, mefenamic acid, flufenamic acid, indomethacin, diclofenac, alclofenac, diclofenac sodium, ibuprofen, ketoprofen, naproxen, pranoprofen, fenoprofen, sulindac, fenclofenac, clidanac, flurbiprofen, fentiazac, bufexamac, piroxicam, phenylbutazone, oxyphenbutazone, clofezone, pentazocine, mepirizole, tiaramide hydrochloride, hydrocortisone, predonisolone, dexamethasone, triamcinolone acetonide, fluocinolone acetonide, hydrocortisone acetate, predonisolone acetate, methylpredonisolone, dexamethasone acetate, betamethasone, betamethasone valerate, flumetasone, fluorometholone, beclomethasone diproprionate, and combinations thereof.

Further, examples of anti-histamines include, but are not limited to, diphenhydramine hydrochloride, diphenhydramine salicylate, diphenhydramine, chlorpheniramine hydrochloride, chlorpheniramine maleate isothipendyl hydrochloride, tripelennamine hydrochloride, promethazine hydrochloride, methdilazine hydrochloride, and combinations thereof.

Still further, examples of local anesthetics include, but are not limited to, dibucaine hydrochloride, dibucaine, lidocaine hydrochloride, lidocaine, benzocaine, p-buthylaminobenzoic acid 2-(di-ethylamino) ethyl ester hydrochloride, procaine hydrochloride, tetracaine, tetracaine hydrochloride, chloroprocaine hydrochloride, oxyprocaine hydrochloride, mepivacaine, cocaine hydrochloride, piperocaine hydrochloride, dyclonine, dyclonine hydrochloride, and combinations thereof.

Examples of bactericides and disinfectants include, but are not limited to, thimerosal, phenol, thymol, benzalkonium chloride, benzethonium chloride, chlorhexidine, povidone iodine, cetylpyridinium chloride, eugenol, trimethylammonium bromide, benzoic acid, sodium benzoate, and combinations thereof. Examples of vasoconstrictors include, but are not limited to, naphazoline nitrate, tetrahydrozoline hydrochloride, oxymetazoline hydrochloride, phenylephrine hydrochloride, tramazoline hydrochloride, and combinations thereof.

Also, examples of hemostatics include, but are not limited to, thrombin, phytonadione, protamine sulfate, aminocaproic acid, tranexamic acid, carbazochrome, carbaxochrome sodium sulfanate, rutin, hesperidin, and combinations thereof. Examples of chemotherapeutic drugs include sulfamine, sulfathiazole, sulfadiazine, homosulfamine, sulfisoxazole, sulfisomidine, sulfamethizole, nitro furazone, taxanes, platinum compounds, topoisomerase I inhibitors, anthrocycline, and combinations thereof.

Additionally, examples of antibiotics include, but are not limited to, penicillin, methicillin, oxacillin, cefalotin, cefalordin, erythromycin, lincomycin, tetracycline, chlortetracycline, oxytetracycline, metacycline, chloramphenicol, kanamycin, streptomycin, gentamicin, bacitracin, cycloserine, clindamycin, vancomycin, and combinations thereof. Examples of keratolytics include, but are not limited to, salicylic acid, podophyllum resin, podolifox, cantharidin, and combinations thereof. Examples of cauterizing agents include, but are not limited to, chloroacetic acids, silver nitrate, and combinations thereof.

Further, examples of hormones include, but are not limited to, estrone, estradiol, testosterone, equilin, human growth hormone, and combinations thereof. Examples of analgesic narcotics include, but are not limited to, ibuprofen, ketoprofen, acetaminophen, acetylsalicylic acid, fentanyl, buprenorphine, codeine sulfate, levorphanol, morphine hydrochloride, and combinations thereof.

Examples of anti-virals include, but are not limited to, protease inhibitors, thymidine kinase inhibitors, sugar and glycoprotein synthesis inhibitors, structural protein synthesis inhibitors, attachment and adsorption inhibitors, nucleoside analogues such as acyclovir, penciclovir, valacyclovir, and ganciclovir, and combinations thereof.

In yet another embodiment, the pharmaceutical includes essential oils used in Listerine® mouthwash, commercially available from Pfizer Inc. of New York, N.Y. In a further embodiment, the pharmaceutical includes active ingredients in Chloraseptic®, commercially available from Prestige Brands, Inc. of Irvington, N.Y. In an additional embodiment, the pharmaceutical includes active ingredients in Triaminic®, commercially available from Novartis International AG, of Basel, Switzerland. In yet another embodiment, the medicament is selected from the group of ibuprofen, diphenhydramine hydrochloride, and combinations thereof.

In all embodiments of both the composition and the film (10), the medicament is preferably present in at least a minimum effective dose, as determined by one skilled in the art. In one embodiment of the composition, the medicament is preferably present in an amount of from 0.5 to 30, more preferably of from 1 to 25, and most preferably of from 2 to 10, % (w/w) solid of the composition. In another embodiment of the composition, the medicament is preferably present in an amount of from 50 to 2000, more preferably of from 100 to 1000, and most preferably of from 500 to 1000, mg per 10 grams of the composition. In the film, the medicament is preferably present in an amount of from 0.1 to 30, more preferably of from 1 to 25, and most preferably of from 5 to 20, mg. In one embodiment, the medicament is present in an amount of from 0.1 to 30 mg per 0.005 to 0.150 grams of a 2.15 cm by 3.3 cm sample of the film (10). In the film (10), the medicament is preferably dispersed in the polymer component. Preferably, the medicament is homogenously dispersed in the polymer component.

Referring now to the polymer component and the polyvinylpyrrolidone having a weight average molecular weight of at least 700,000, the polyvinylpyrrolidone preferably includes the general structure:

wherein x may be any integer so long as the weight average molecular weight is at least 700,000 g/mol. The polyvinylpyrrolidone also preferably has a K value of from 81 to 97.2, as determined by a USP/EP specification, known in the art. The polyvinylpyrrolidone is commercially available from BASF Corporation of Florham Park, N.J. under the trade name of Kollidon®. A particularly suitable polyvinylpyrrolidone has a weight average molecular weight of from 700,000 to 1,000,000 g/mol and includes Kollidon® K-90 having an approximate weight average molecular weight of 1,000,000 g/mol. Other suitable polyvinylpyrrolidones are commercially available from International Specialty Products of Wayne, N.J., under the trade name of Plasdone.

The polymer component may be included in the composition and/or film (10) in any amount so long as the medicament is present in at least the minimum effective dose, as first introduced above. In one embodiment of the composition, the polymer component is preferably included in an amount of from 0.1 to 99.9, more preferably of from 10 to 90, and most preferably in an amount of from 10 to 50, parts by weight per 100 parts by weight of the composition. In one embodiment of the film (10), the polymer component is also preferably included in an amount of from 0.1 to 99.9, more preferably of from 10 to 90, and most preferably in an amount of from 10 to 50, parts by weight per 100 parts by weight of the film (10). In each of the composition and the film (10), the polymer component may consist essentially of the polyvinylpyrrolidone.

Preferably, the composition and the film (10) are substantially free of cellulose including, but not limited to, hydroxyethyl cellulose, hydroxypropyl cellulose, hydroxyethylmethyl cellulose, hydroxypropylmethyl cellulose, microcrystalline cellulose, and combinations thereof. It is to be understood that substantially free, as related to the present invention, preferably includes an amount of cellulose in the composition and/or film (10) of less than 1, more preferably of less than 0.50, and most preferably of less than 0.05, parts by weight per 100 parts by weight of the composition and/or film (10), respectively. In one embodiment, each of the composition and the film (10) are totally free of cellulose, respectively.

The polymer component in the composition and/or the film (10) may further include an auxiliary polymer selected from the group of polyvinylacetates, polyvinylpyrrolidones having weight average molecular weights of less than 700,000 g/mol, polyalkylacrylates, polyvinylalcohols, and combinations thereof. If included in the composition and/or the film (10), the auxiliary polymer may be included in any amount and preferably in an amount of from 0.1 to 50, more preferably from 5 to 25, and most preferably of from 5 to 10, parts by weight per 100 parts by weight of the polymer component.

If the auxiliary polymer includes the polyvinylacetate, the polyvinylacetate may be copolymerized with the polyvinylpyrrolidone having the weight average molecular weight of less than 700,000 g/mol. If so, the copolymerized polyvinylacetate and polyvinylpyrrolidone is commercially available from BASF Corporation of Florham Park, N.J. under the trade name of Kollidon® VA64 (Copovidone), and may include the general structure:

wherein x and y are integers between 4 and 6. If included in the polymer component, the polyvinylacetate may be included in any amount and preferably in an amount of from 0.1 to 50, more preferably of from 0.1 to 30, and most preferably in an amount of from 0.1 to 20, parts by weight per 100 parts by weight of the auxiliary polymer.

Alternatively, the polyvinylacetate may be separate from the polyvinylpyrrolidone having the weight average molecular weight of less than 700,000 g/mol, (i.e., not copolymerized with the polyvinylpyrrolidone). If separate and not copolymerized, the polyvinylacetate and polyvinylpyrrolidone are commercially available from BASF Corporation of Florham Park, N.J. under the trade name of Kollidon® SR and may include the general structure:

wherein the integers x and y are integers between 2 and 8. Also, if separate and not copolymerized, the polyvinylacetate and polyvinylpyrrolidone may be included in any amount and preferably in an amount of from 0.1 to 50, more preferably of from 0.1 to 30, and most preferably in an amount of from 0.1 to 20, parts by weight per 100 parts by weight of the auxiliary polymer. It is also contemplated that the auxiliary polymer may include both the copolymerized polyvinylacetate and polyvinylpyrrolidone and the separate and not copolymerized polyvinylacetate and polyvinylpyrrolidone.

If the auxiliary polymer includes the polyvinylpyrrolidone having the weight average molecular weight of less than 700,000 g/mol, the polyvinylpyrrolidone preferably includes the general structure:

wherein x may be any integer so long as the weight average molecular weight is less than 700,000 g/mol. Suitable polyvinylpyrrolidones having weight average molecular weights of less than 700,000 g/mol are commercially available from BASF Corporation of Florham Park, N.J. under the trade name of Kollidon® and include, but are not limited to, Kollidon® K12, Kollidon® K17, Kollidon® K25, Kollidon® K30, and combinations thereof. If the auxiliary polymer includes the polyvinylpyrrolidone having the weight average molecular weight of less than 700,000 g/mol (without the polyvinylacetate), the polyvinylpyrrolidone may be included in any amount and preferably in an amount of from 0.1 to 50, more preferably of from 0.1 to 30, and most preferably in an amount of from 0.1 to 20, parts by weight per 100 parts by weight of the auxiliary polymer.

If the auxiliary polymer includes the polyalkylacrylate (e.g., polymethylacrylate), the polyalkylacrylate is commercially available from BASF Corporation of Florham Park, N.J. under the trade name of Kollicoat® MAE 100P. Preferably, the polyacrylate includes the general structure:

wherein x and y are integers between 1 and 2. If the auxiliary polymer includes the polyalkylacrylate, the polyalkylacrylate is preferably may be included in any amount and preferably in an amount of from 0.1 to 50, more preferably of from 0.1 to 20, and most preferably in an amount of from 0.1 to 10, parts by weight per 100 parts by weight of the auxiliary polymer. If included, the polyalkylacrylate may delay a dissolution time of the film (10) due to an acrylic nature of the polyalkylacrylate. Specifically, the polyacrylate may optimally be included in the composition and/or the film (10) when application of the composition and/or film (10) includes an environment having a pH of greater than 5.

If the auxiliary polymer includes polyvinylalcohol (PVA), the polyvinylalcohol may be a component of commercially available copolymers from BASF Corporation of Florham Park, N.J. under the trade names of Kollicoat® IR, Kollicoat® IR White and Kollicoat® Protect. Preferably, the polyvinylalcohol includes polyethylene grafted (PEG) polyvinylalcohol and includes the general structure:

wherein x and y are integers between 1 and 3. If the auxiliary polymer includes the polyvinylalcohol, and specifically the polyethylene grafted polyvinylalcohol, the polyvinylalcohol may be included in any amount and preferably in an amount of from 0.1 to 50, more preferably of from 0.1 to 30, and most preferably in an amount of from 0.1 to 20, parts by weight per 100 parts by weight of the auxiliary polymer.

It is also contemplated that the auxiliary polymer may include the polyvinylpyrrolidone, the polyalkylacrylate, and the polyvinylalcohol. If so, the polyvinylpyrrolidone may be included in any amount and preferably in an amount of from 0.1 to 50, more preferably of from 0.1 to 30, and most preferably of from 0.1 to 20, parts by weight per 100 parts by weight of the auxiliary polymer. Also, the polyalkylacrylate may be included in any amount and preferably in an amount of from 0.1 to 50, more preferably of from 0.1 to 20, and most preferably of from 0.1 to 10, parts by weight per 100 parts by weight of the auxiliary polymer. Further, the polyvinylalcohol, and specifically the polyethylene grafted polyvinylalcohol, may be included in any amount and preferably in an amount of from 0.1 to 50, more preferably of from 0.1 to 30, and most preferably of from 0.1 to 20, parts by weight per 100 parts by weight of the auxiliary polymer. It is further contemplated that the auxiliary polymer may include both the copolymerized polyvinylacetate and polyvinylpyrrolidone, the separate and not copolymerized polyvinylacetate and/or polyvinylpyrrolidone, and either or both of the polyvinylpyrrolidone having the weight average molecular weight of less than 700,000 g/mol, the polyacrylate, and the polyvinylalcohol, in amounts and combinations determined by one skilled in the art.

The composition and the film (10) may also include an additive selected from the group of a plasticizer, an anti-tacky agent, a masking agent, an antioxidant, an excipient, a sweetener, a colorant, an emulsifier, a saliva stimulating agent, a cooling agent, a stabilizing agent, a binding agent, a fragrance, and combinations thereof. The additive may be present in the composition in any amount and is preferably present in an amount of from 0.1 to 10, more preferably of from 0.1 to 5, and most preferably of from 0.1 to 2, parts by weight per 100 parts by weight of the composition. Similarly, in the film (10), the additive may be present in the film (10) in any amount and is preferably present in an amount of from 0.1 to 10, more preferably of from 0.1 to 5, and most preferably of from 0.1 to 2, parts by weight per 100 parts by weight of the film (10).

Examples of suitable plasticizers as an additive include, but are not limited to, monoacetin, diacetin, triacetin, polysorbate 80, triethylcitrate, polyethylene glycol 300, polyethylene glycol 400, polyethylene glycol 600, and combinations thereof. Examples of suitable masking agents as an additive include, but are not limited to, poloxamers, polyoxyl-based saturated and unsaturated chain castor oils such as Cremophor EL, Cremophor RH40, and Cremophor RH60, and combinations thereof. Examples of suitable antioxidants as an additive include, but are not limited to, sodium metabisulfite, sodium sulfite, sodium formaldehyde sulfoxylate, sodium formaldehyde sulfoxylate with ethylenediamine tetraacetic acid (EDTA), sodium thiosulfate, acetylcysteine, thioglycerol, butylated hydroxy anisole (BHA), butylated hydroxy toluene (BHT), alpha.-tocopherol, monoethanolamine, triethanolamine, citric acid, tartaric acid, EDTA, EDTA with citric acid, EDTA with BHA, EDTA with sodium metabisulfite, and triethanolamine with BHA, and combinations thereof. Examples of suitable excipients as an additive include, but are not limited to, aspartame, aspartic acid, benzyl alcohol, cetyl alcohol, dextrans, detrates, dextrins, dextrose, fructose, gelatin, glycerin, glycols, metal oxides and dioxides, kaolin, lactilols, lactose, mannitol, sorbates, starches, stearates, sucrose, and combinations thereof.

Examples of suitable flavorants as an additive include, but are not limited to, natural and/or artificial flavorants such as oils and aromatics, oleo resins and extracts derived from plants, leaves, flowers, and fruits, spearmint oil, cinnamon oil, peppermint oil, clove oil, bay oil, thyme oil, cedar leaf oil, oil of nutmeg, oil of sage, and oil of bitter almonds, vanilla, chocolate, coffee, cocoa and citrus oil, including lemon, orange, grape, lime and grapefruit and fruit essences including apple, pear, peach, strawberry, raspberry, cherry, plum, pineapple, apricot, aldehydes and esters including cinnamyl acetate, cinnamaldehyde, citral, diethylacetal, dihydrocarvyl acetate, eugenyl formate, p-methylanisole, acetaldehyde (apple), benzaldehyde (cherry, almond), cinnamic aldehyde (cinnamon), citral, i.e., alpha citral (lemon, lime), neral, i.e. beta citral (lemon, lime), decanal (orange, lemon), ethyl vanillin (vanilla, cream), heliotropine, i.e., piperonal (vanilla, cream), vanillin (vanilla, cream), alpha-amyl cinnamaldehyde, butyraldehyde (butter, cheese), valeraldehyde (butter, cheese), citronellal, decanal (citrus fruits), aldehyde C-8 (citrus fruits), aldehyde C-9 (citrus fruits), aldehyde C-12 (citrus fruits), 2-ethyl butyraldehyde (berry fruits), hexenal, i.e. trans-2 (berry fruits), tolyl aldehyde (cherry, almond), veratraldehyde (vanilla), 2,6-dimethyl-5-heptenal, i.e. melonal (melon), 2-6-dimethyloctanal (green fruit), 2-dodecenal (citrus, mandarin), and combinations thereof.

Examples of suitable sweeteners as an additive include, but are not limited to, monosaccharides, disaccharides and polysaccharides such as xylose, ribose, glucose (dextrose), mannose, galactose, fructose (levulose), sucrose (sugar), maltose, invert sugar (a mixture of fructose and glucose derived from sucrose), partially hydrolyzed starch, corn syrup solids, dihydrochalcones, monellin, steviosides, glycyrrhizin, water-soluble artificial sweeteners such as soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, a potassium salt of 3,4-dihydro-6-methyl-1,2,3-oxathiazine-4-one-2,2-dioxide (acesulfame-K), and a free acid form of saccharin, dipeptide based sweeteners, such as L-aspartic acid derived sweeteners, such as L-aspartyl-L-phenylalanine methyl ester (aspartame), L-alpha-aspartyl-N-(2,2,4,4-tetramethyl-3-thietanyl)-D-alaninamide hydrate, methyl esters of L-aspartyl-L-phenylglycerin and L-aspartyl-L-2,5,dihydrophenyl-glycine, L-aspartyl-2,5-dihydro-L-phenylalanine, L-aspartyl-L-(1-cyclohexyen)-alanine, water-soluble sweeteners derived from naturally occurring water-soluble sweeteners, such as a chlorinated derivatives of ordinary sugars, and protein based sweeteners such as Thaumatin I and II, and combinations thereof.

Examples of suitable colorants as an additive include, but are not limited to, FD&C dyes and lakes such as FD&C Blue No. 2, which is the disodium salt of 5,5-indigotindisulfonic acid, Green No. 3 dye, which is a triphenylmethane dye and is the monosodium salt of 4-[4-N-ethyl-p-sulfobenzylamino) diphenyl-methylene]-[1-N-ethyl-N-p-sulfonium benzyl)-2, 5-cyclo-hexadienimine], and combinations thereof. Examples of suitable emulsifiers include, but are not limited to, triethanolamine stearate, quaternary ammonium compounds, acacia, gelatin, lecithin, bentonite, veegum, and combinations thereof. Examples of suitable saliva stimulating agents as an additive include, but are not limited to, food acids such as citric acid, lactic acid, malic acid, succinic acid, ascorbic acid, adipic acid, fumaric acid, tartaric acid, and combinations thereof. An example of a suitable cooling agent includes, but is not limited to, monomenthyl succinates. Examples of suitable stabilizing agents include, but are not limited to, xanthan gum, locust bean gum and carrageenan, and combinations thereof. An example of a suitable binding agent includes, but is not limited to, starch. Examples of suitable fragrances as an additive include, but are not limited to, cinnamon, chocolate, amber, rose, vanilla, bubble gum, coffee, mint, honey, fruit flavors such as apple, strawberry, banana, cherry, cranberry, watermelon, guava, mango, papaya, pineapple, and blueberry, and combinations thereof.

Additionally, the composition may include a solvent. The solvent may be any solvent known in the art to dissolve or partially dissolve the polymer component and the medicament. Particularly suitable solvents have boiling points from 30 to 100° C. and may include, but are not limited to, ethanol, methanol, 2-propanol, butanol, ethyl acetate, acetone, methylene chloride, tetrahydrofuran, chloroform, water, and combinations thereof. As first introduced above, the composition has a viscosity of from of from 500 to 5,000 cps at 25° C., with or without any solvent. In one embodiment, the composition includes the solvent and has a viscosity of from 1,500 to 3,500 cps at 25° C. In another embodiment, the composition also includes the solvent and has a viscosity of from 1,000 to 3,500 centipoises at 25° C. Preferably, the film (10) is substantially free of the solvent and most preferably is totally free of the solvent. It is to be understood that substantially free, as related to the present invention, preferably includes an amount of solvent in the film (10) of less than 1, more preferably of less than 0.50, and most preferably of less than 0.05, parts by weight per 100 parts by weight of the film (10), respectively.

Referring specifically to the film (10), the film (10) preferably includes a single (mono) layer (i.e., the film (10) is a monolayer film (10)). However, the film (10) may include more than one layer so long as the medicament is dispersed within the polymer component. In one embodiment, the film is shaped as strips. The film (10) is preferably solid at room temperature and may have any shape, surface area, and thickness. Preferably, the film (10) has a thickness of from 1 to 100, more preferably of from 10 to 50, and most preferably of from 10 to 40, microns. The film (10) also preferably has a weight of from 5 to 100, more preferably of from 10 to 90, and most preferably of from 10 to 80, mg. The film (10) further preferably has a surface area of from 1 to 20, more preferably of from 2 to 20, and most preferably of from 5 to 10, square centimeters, as needed for film quality to meet patience compliance, as is known in the art.

In one embodiment, the film (10) preferably has a flexibility, i.e., elongation, of less than or equal to 500, more preferably of from 100 to 500, and most preferably of from 300 to 500, percent, as determined by an elongation test. However, the film (10) may have any flexibility depending on application as selected by one skilled in the art. Elongation is a measurement of a fractional increase in length of samples of the film (10) stressed under tension. The elongation is measured utilizing a procedure wherein samples of the film (10) are subjected to a manual stress test. Approximately equal stresses are manually applied to opposite ends of 2.15 cm by 3.3 cm rectangular samples of the film (10). The approximately equal stresses are applied such that the samples of the film (10) are stressed to breaking. The percentage increase in length of the samples of the film (10) before breaking is recorded as the elongation.

In another embodiment, the film (10) preferably has a dissolution time of less than or equal to 300 seconds, more preferably of from 5 to 300 seconds, and most preferably of from 5 to 60 seconds, as determined by a dissolution time test. However, the film (10) may have any dissolution time depending on application as selected by one skilled in the art. Dissolution time is a time measured for samples of the film (10) to change state from a solid state to a state in which any residue is a soft mass having no palpably firm core. The dissolution time is measured utilizing a procedure wherein 2.15 cm by 3.3 cm samples of the film (10) are placed into 100 ml of deionized water and stirred at a rate of 100 rpm using a PMC Dataplate stirrer at room temperature. The determination of the dissolution time is made visually.

In another embodiment, the film (10) preferably has a loading ability of approximately 25, more preferably of from 5 to 25, and most preferably of from 10 to 25, mg of medicament, as determined by a loading ability test, as is known in the art. However, the film (10) may have any loading ability depending on application as selected by one skilled in the art. Loading ability is a measurement of a maximum amount of the medicament that can be included in samples of the films (10). The loading ability is dependent on a size and thickness of the film (10) and amount of medicament in the composition.

In a further embodiment, the film (10) may have a tackiness of from 1 to 5, more preferably of from 1 to 3, and most preferably of from 1 to 2, as determined by a tackiness test. However, the film (10) may have any tackiness depending on application as selected by one skilled in the art. Tackiness is a tactile measurement of a "stickiness" of samples of the film (10). Tackiness is tactilely measured by pressing samples of each of the films (10) with the fingers to manually assess the stickiness of each of the samples. The stickiness is measured on a scale of one to five, with 5 representing maximum stickiness and 1 representing minimum or no stickiness.

The film (10) may also be dispensed in an article (12) (i.e., the article (12) may include the film (10)), as shown in FIG. 1b. Two particularly suitable articles (12) are disclosed in U.S. Des. Pat. No. D423,302 and U.S. Pat. No. 6,726,054, hereby expressly incorporated by reference. However, the article (12) may include any known in the art for dispensing films (10).

Referring now to the method of forming the film (10), the method includes the steps of providing the medicament and providing the polymer component. In one embodiment, the step of providing the polymer component is further defined as providing a polymer component consisting essentially of the polyvinylpyrrolidone having the weight average molecular weight of at least 700,000 g/mol. In another embodiment, the step of providing the polymer component is further defined as providing a polymer component having a weight average molecular weight of from 700,000 to 1,000,000 g/mol.

The method also includes the step of combining the polymer component and the medicament to form the composition having the viscosity of from 500 to 5,000 cps at 25° C. In one embodiment, the step of combining is further defined as dispersing the medicament in the polymer component. In another embodiment, the step of combining is further defined as combining the polymer component and the medicament such that the film (10) includes from 0.1 to 30 mg of the medicament per 0.005 to 0.150 grams of a 2.15 cm by 3.3 cm sample of the film (10). However, as first introduced above, the medicament may be included in any amount and is preferably included in at least a minimum effective dose, as determined by one skilled in the art.

In another embodiment, the method includes the steps of providing the solvent and combining the medicament carrier composition and the solvent. In yet another embodiment, the method includes the step of applying the medicament carrier composition onto a surface of a mold. It is contemplated that the mold may be an open mold or may be a closed mold. In yet another embodiment, the method includes the step of applying the medicament carrier composition onto a backing layer. Preferably, the backing layer is disposed on the surface of the mold. The backing layer may include a backing polymer selected from the group of mylar, polyethylene terephthalate, and combinations thereof. However, the backing polymer and/or the backing layer may be any known in the art and may be appropriately selected by one of skill in the art. It is to be understood that the backing layer is not integral with the film (10) and is not considered a layer of the film (10).

The method also includes the step of drying the medicament carrier composition to form the film (10). In one embodiment, the step of drying is further defined as drying at a temperature of from 30 to 90° C. and for a time of from 10 to 30 minutes. In another embodiment, the step of drying is further defined as drying at a temperature of from 20 to 100° C., more preferably of from 30 to 90, and most preferably of from 40 to 60° C. In yet another embodiment, the step of drying preferably is further defined as drying for a time of from 5 to 40 minutes, more preferably of from 10 to 30 minutes, and most preferably of from 10 to 25 minutes. In an additional embodiment, the step of drying is further defined as drying the composition to form the film (10) having a thickness of from 10 to 50 microns and a surface area of from 2 to 20 square centimeters. In yet an additional embodiment, the step of drying is further defined as drying to form a film (10) having a monolayer. The method includes the step of drying to evaporate the solvent from the composition. Preferably all of the solvent is evaporated such that the viscosity of the composition is reduced when the film (10) is formed. It is to be understood that both the temperature and time of drying are dependent on the boiling point of the solvent. As such, the step of drying may occur at any temperature and for any time, as selected by one skilled in the art. Additionally, the step of drying may be further defined as drying the composition to form the film (10) having a thickness of from 10 to 50 microns and a surface area of from 2 to 20 square centimeters. However, as first introduced above, the film (10) may have any surface area and thickness.

In another embodiment, the method may further include the step of cutting the film (10) into strips. The strips preferably have a size that easily fits into an oral cavity. However, it is contemplated that the strips may have any size. In the most preferred embodiment, the strips are 2.15 cm by 3.3 cm.

EXAMPLES

A first series of medicament carrier compositions, Compositions 1 through 5, are formed according to the present invention and are measured for viscosity. To form each of the Compositions 1 through 5, a Polymer Component including a polyvinylpyrrolidone having a weight average molecular weight of at least 700,000 g/mol is added to a vessel at room temperature and dissolved in ethanol and/or water, as set forth in Table 1 below.

To form Composition 1, a first and a second additive, Additive 1 and Additive 2, are added to the vessel with the Polymer Component, while stirring at a rate of 1000 rpm, over a time of two hours, and at room temperature. To form Composition 2, a first auxiliary polymer, Auxiliary Polymer 1, is added to the vessel with the Polymer Component, while stirring at a rate of 1000 rpm, over a time of three hours, and at room temperature. To form Composition 3, a second auxiliary polymer, Auxiliary Polymer 2, is added to the vessel with the Polymer Component, while stirring at a rate of 1000 rpm, over a time of three hours, and at room temperature. To form Composition 4, a third auxiliary polymer, Auxiliary Polymer 3, is added to the vessel with the Polymer Component, while stirring at a rate of 1000 rpm, over a time of three hours, and at room temperature. To form Composition 5, a fourth auxiliary polymer, Auxiliary Polymer 4, is added to the vessel with the Polymer Component, while stirring at a rate of 1000 rpm, over a time of three hours, and at room temperature. Each of the Auxiliary Polymers 1 through 4 are stirred with the Polymer Component with both a Propeller IKA mixer commercially available from VWR Scientific Products of Bridgeport, N.J. and an SRT1 roller mixer commercially available from Jenkins of Bridgeville, Pa.

Amounts of the Auxiliary Polymers 1 through 4, and the Additives 1 and 2, are set forth in Table 1 below. After formation, each of the Compositions 1 through 5 is evaluated for viscosity using a Brookfield DV-II Viscometer commercially available from Brookfield Engineering of Middleboro, Mass. In Table 1, parts are by weight unless otherwise noted.

TABLE 1

| | Composition 1 | Composition 2 | Composition 3 | Composition 4 | Composition 5 |
|---|---|---|---|---|---|
| Polymer Component | 15 | 13.64 | 12.45 | 13.64 | 13.27 |
| Ethanol | 84.5 | 82.27 | 85.47 | 76.81 | 80.08 |
| Water | 0 | 2.73 | 0 | 8.18 | 5.31 |
| Auxiliary Polymer 1 | 0 | 0.91 | 0 | 0 | 0 |
| Auxiliary Polymer 2 | 0 | 0 | 1.66 | 0 | 0 |
| Auxiliary Polymer 3 | 0 | 0 | 0 | 0.91 | 0 |
| Auxiliary Polymer 4 | 0 | 0 | 0 | 0 | 0.88 |
| Additive 1 | 0.5 | 0.45 | 0.41 | 0.45 | 0.44 |
| Additive 2 | 0.01 | 0.01 | 0.01 | 0.01 | 0.01 |
| Viscosity (cps at 23° C.) | 1920 | >5,000 | 2200 | 3380 | 2410 |

Polymer Component, commercially available from BASF Corporation of Florham Park, N.J. under the trade name of Kollidon® 90F, is a N-vinylpyrrolidone (NVP) homopolymer.

Ethanol is absolute ethanol commercially available from Sigma Aldrich Corporation of St. Louis, Mo.

Auxiliary Polymer 1, commercially available from BASF Corporation of Florham Park, N.J. under the trade name of Kollicoat® MAE 100P, is a methacrylic acid ethyl acrylate copolymer.

Auxiliary Polymer 2, commercially available from BASF Corporation of Florham Park, N.J. under the trade name of Kollidon® VA64, is a vinylpyrrolidone-vinyl acetate copolymer.

Auxiliary Polymer 3, commercially available from BASF Corporation of Florham Park, N.J. under the trade name of Kollicoat® IR, is a polyethylene glycol grafted polyvinylalcohol.

Auxiliary Polymer 4, commercially available from BASF Corporation of Florham Park, N.J. under the trade name of Kollidon® SR, is a polyvinyl acetate and polyvinylpyrrolidone copolymer.

Additive 1, commercially available from BASF Corporation of Florham Park, N.J. under the trade name of Lutrol® E 400, is polyethylene glycol.

Additive 2, commercially available from Spectrum Chemical Mfg. Corp of Gardena, Calif., under the trade name of FD&C Red #40, is 6-hydroxy-5-[(2-methoxy-5-methyl-4-sulfophenyl)azo]-2-naphthalenesulfonic acid.

The results of the determination of the viscosity indicate that each of the Compositions 1 through 5 has a viscosity that allows them to be used to form films that have a consistent thickness and size such that the films are not defective and alteration of sizes and shapes of the films and recycling of the films for re-processing are not needed. Specifically, the viscosity determinations suggest that each of the Compositions 1 through 5 adequately adhere to the backing layer allowing for effective formation of the films.

A series of monolayer films, Films 1 through 5, are also formed and correspond to the Compositions 1 through 5, respectively. Specifically, to form the Films 1 through 5, each of the Compositions 1 through 5 is poured on a release liner lining an open mold. The release liner is commercially available from 3M of St. Paul, Minn. under the trade name of Scotchpak® 1022. After each of the Compositions 1 through 5 are poured into the liner, the Compositions are "drawn-down" to desired thicknesses using an applicator edged at 5 to 50 mils, commercially available from the Paul N. Gardner Company, Inc, of Pompano Beach, Fla. After each is drawn down, the Compositions 1 through 5 are dried to form the Films 1 through 5, as set forth in Table 2 below. The Compositions 1 through 5 are dried in an oven at 50° C. for differing times according to the desired thicknesses. The oven is commercially available from Lindberg/Blue M of Asheville, N.C. After formation, the Films 1 through 5 are cut into 2.15 cm by 3.3 cm strips using a die board prepared by Bomar Die Company of Millville, N.J. on a Carver Press and measured for thickness using a Mitutoyo digimatic indicator, as also set forth in Table 2 below. After cutting, the strips are measured for dissolution time, as first described above and as set forth in Table 2 below.

TABLE 2

| | Film 1 | Film 2 | Film 3 | Film 4 | Film 5 |
|---|---|---|---|---|---|
| Dissolution Time (sec) | 33 | 56.7 | 29 | 33 | 31.7 |
| Thickness (mils) | 78 | 80 | 80 | 80 | 80 |
| Drying Time (min) | 15-25 | 15-25 | 15-25 | 15-25 | 15-25 |

Figure 2:
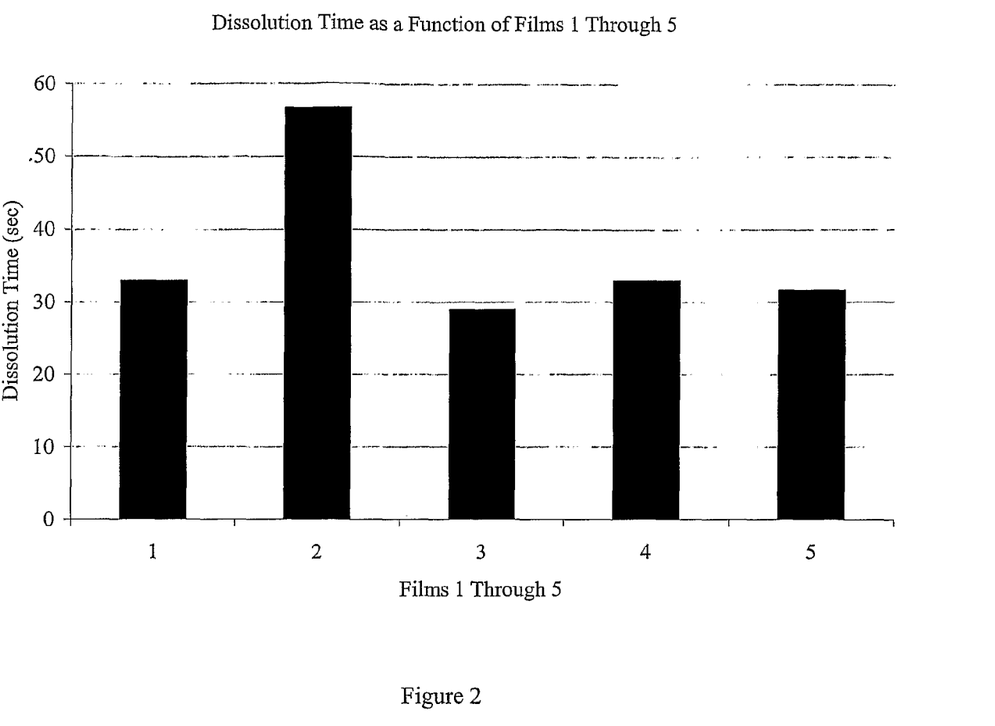
FIG. 2 is a bar graph illustrating Dissolution Time as a Function of Films 1 through 5.

The results of the determination of Dissolution Time indicate that the samples of the Films 1 and 3 through 5 exhibit decreased Dissolution Times as compared to the sample of Film 2. These differences in Dissolution Times may be the result of an acrylic nature of the Kollicoat® MAE 100P, as the Auxiliary Polymer 1, which requires a pH higher than 5 for dissolution, which is significant as the pH of saliva is approximately between 5 and 7.

A second series of medicament carrier compositions, Compositions 6 through 8, are also formed according to the present invention and are measured for viscosity using the Brookfield DV-II Viscometer commercially available from Brookfield Engineering of Middleboro, Mass. The Compositions 6 through 8 are generally formed in the same way as the Compositions 1 through 5 in that the Polymer Component including the polyvinylpyrrolidone having a weight average molecular weight of at least 700,000 g/mol is added to a vessel and dissolved in ethanol, as set forth in Table 3 below.

Specifically, to form Composition 6, the Additives 1 and 2, and additional additives, Additives 3 and 4, are added to the vessel in addition to the Polymer Component while stirring at a rate of 1000 rpm, over a time of three hours, and at room temperature. Also, to form Composition 7, Ibuprofen is added to the vessel in addition to the Additives 1 through 4 and the Polymer Component while stirring at a rate of 1000 rpm, over a time of four hours, and at room temperature. To form Composition 8, Diphenhydramine Hydrochloride is added to the vessel in addition to the Additives 1 through 4 and the Polymer Component while stirring at a rate of 1000 rpm, over a time of four hours, and at room temperature. Amounts of the Polymer Component, the Ethanol, the Additives 1 through 4, the Ibuprofen, and the Diphenhydramine Hydrochloride, used to form the Compositions 6 through 8, are set forth in Table 3 below. In Table 3, all parts are by weight unless otherwise noted.

TABLE 3

|  | Composition 6 | Composition 7 | Composition 8 |
|---|---|---|---|
| Polymer Component | 14.86 | 13.52 | 13.52 |
| Ethanol | 84.23 | 76.63 | 76.63 |
| Additive 1 | 0.52 | 0.47 | 0.47 |
| Additive 2 | 0.01 | 0.01 | 0.01 |
| Additive 3 | 0.2 | 0.18 | 0.18 |
| Additive 4 | 0.2 | 0.18 | 0.18 |
| Ibuprofen | 0 | 9.02 | 0 |
| Diphenhydramine Hydrochloride | 0 | 0 | 9.02 |
| Viscosity (cps at 23° C.) | 1920 | 1690 | 2250 |

Additive 3, commercially available from McNeil Nutritionals, LLC of Ft. Washington Pa., under the trade name of Sucralose, is 1,6-dichloro-1,6-dioxy-β-D-fructo-furanosyl-4-chloro-4-deoxy-α-D-galactopyranoside.

Additive 4, commercially available from BASF Corporation of Florham Park, N.J. under the trade name of Cremophor RH40, is polyoxyl 40 hydrogenated castor oil.

Ibuprofen is commercially available from BASF Corporation of Florham Park, N.J. under the trade name of Ibuprofen 90.

Diphenhydramine Hydrochloride is commercially available from Sigma Aldrich Corporation of St. Louis, Mo.

The results of the determination of the viscosity for Compositions 6 through 8 indicate that each has a viscosity that allows the Compositions 6 through 8 to be used to form films that have a consistent thickness and size such that alteration of sizes and shapes of the films and recycling of the films for re-processing are not needed.

A second series of monolayer films, Films 6a through 6d, Films 7a through 7d, and Films 8a through 8d, are also formed and correspond to the Compositions 6 through 8, respectively. Specifically, to form the Films 6a through 6d, Films 7a through 7d, and Films 8a through 8d, samples of each of the Compositions 6 through 8 are poured onto the release liner lining the open mold, as first described above. The release liner is commercially available from 3M of St. Paul, Minn. under the trade name of Scotchpak® 1022. After each of the samples of the Compositions 6 through 8 are poured onto the liner, the samples are "drawn-down" to desired thicknesses of 10 to 40 mils using the applicator edged at 5 to 50 mils, commercially available from the Paul N. Gardner Company, Inc of Pompano Beach, Fla. After each is drawn down, the samples of the Compositions 6 through 8 are dried to form the Films 6a through 6d, Films 7a through 7d, and Films 8a through 8d, as set forth in Table 4 below. The samples of the Compositions 6 through 8 are dried in an oven at 50° C. for differing times according to the desired thicknesses. The oven is commercially available from Lindberg/Blue M of Asheville, N.C. After formation, the samples of the Films 6a through 6d, Films 7a through 7d, and Films 8a through 8d are cut into 2.15 cm by 3.3 cm strips using the die board prepared by Bomar Die Company of Millville, N.J. on a Carver Press and measured for thickness using a Mitutoyo digimatic indicator, as also set forth in Table 4 below. After cutting, the strips of the Films 6a through 6d, Films 7a through 7d, and Films 8a through 8d, are measured for dissolution time, elongation, and tackiness, as first described above and as set forth in Table 4 below. Additionally, the strips of the Films 7a through 7d and the Films 8a through 8d are measured for loading ability, as also set forth in Table 4 below.

TABLE 4

|  | Film 6a | Film 6b | Film 6c | Film 6d |
|---|---|---|---|---|
| Dissolution Time (sec) | 11 | 9.3 | 17.7 | 34 |
| Loading Ability (mg medicament) | N/A | N/A | N/A | N/A |
| Elongation (%) | 10 | 10 | 10 | 50 |
| Tackiness (1-5) | 1 | 1 | 1 | 1 |
| Thickness (wet mils) | 10 | 20 | 30 | 40 |

|  | Film 7a | Film 7b | Film 7c | Film 7d |
|---|---|---|---|---|
| Dissolution Time (sec) | 27.3 | 78.3 | 165 | 262.5 |
| Loading Ability (mg medicament) | 6.9 | 13.5 | 19.9 | 21.5 |
| Elongation (%) | 400 | 500 | 500 | 500 |
| Tackiness (1-5) | 1 | 1 | 4 | 5 |
| Thickness (wet mils) | 10 | 20 | 30 | 40 |

|  | Film 8a | Film 8b | Film 8c | Film 8d |
|---|---|---|---|---|
| Dissolution Time (sec) | 5 | 13.3 | 35 | 55 |
| Loading Ability (mg medicament) | 7.9 | 16.7 | 23.2 | 29.9 |
| Elongation (%) | 500 | 500 | 500 | 400 |
| Tackiness (1-5) | 5 | 5 | 5 | 5 |
| Thickness (wet mils) | 10 | 20 | 30 | 40 |

Figure 3:
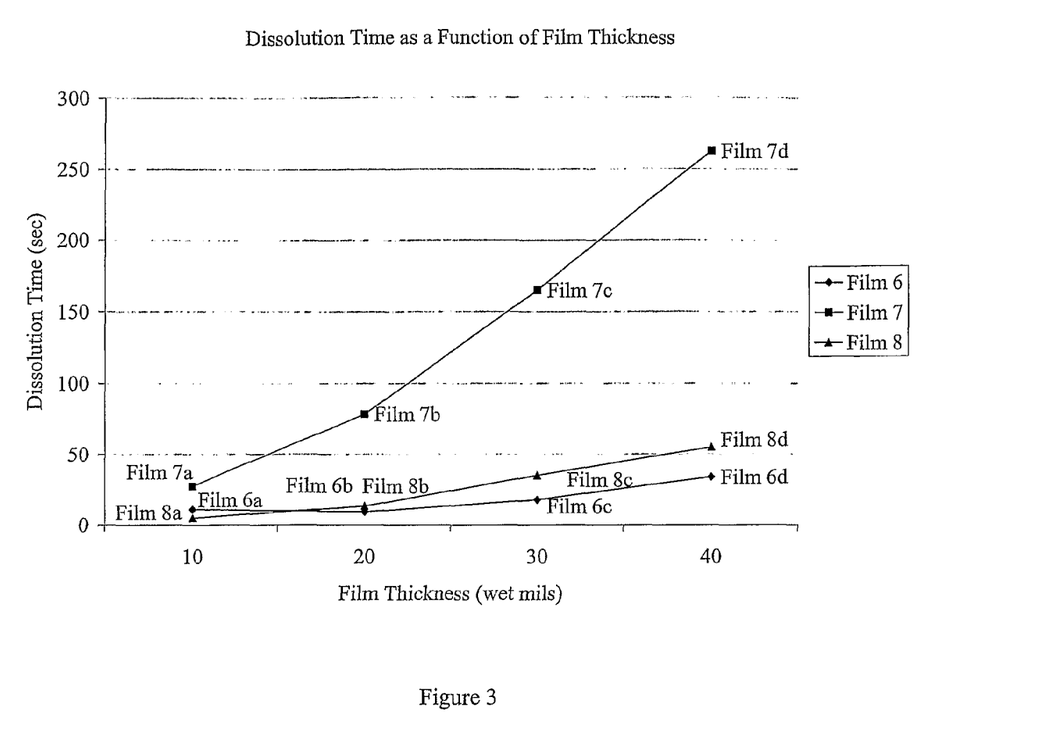
FIG. 3 is a line graph illustrating Dissolution Time as a Function of Film Thickness of Films 6a through 6d, 7a through 7d, and 8a through 8d.

The results of the determination of Dissolution Time indicate that the Films 6a through 6d generally exhibit slowly increasing Dissolution Times with increasing thicknesses. Similarly, the results indicate that the Films 8a through 8d exhibit similar Dissolution Times to those of the Films 6a through 6d. The results indicate that the Films 7a through 7d exhibit more quickly increasing Dissolution Times than the Films 6a through 6d and the Films 8a through 8d. The Films 7a through 7d dissolve at a rate that is much slower than the Films 6a through 6d and the Films 8a through 8d, indicating that the Ibuprofen delays dissolution by possibly providing a coating around the Films 7a through 7d. These results generally indicate that Dissolution Time is dose dependent and the Films including increased doses of the medicament dissolve more slowly than those Films with decreased doses. Therefore, these Films 6a through 6d, 7a through 7d, and 8a through 8d, are ideally suited for dosage development requiring decreased (small) amounts of the medicament, such as in mucoadhesive films.

Figure 4:
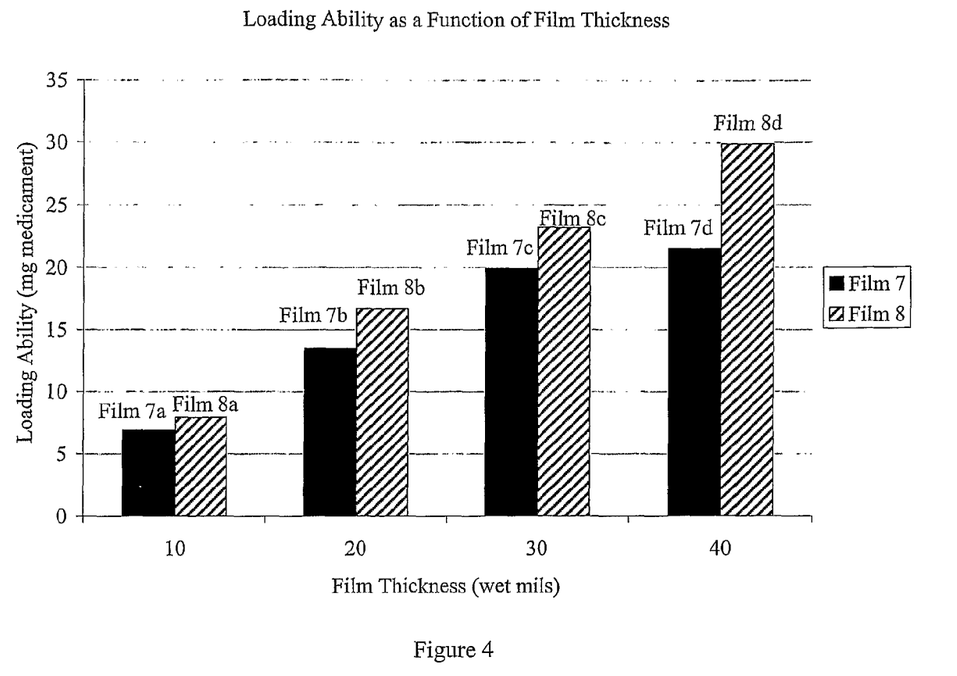
FIG. 4 is a bar graph illustrating Loading Ability as a Function of Film Thickness of Films 7a through 7d and 8a through 8d.

The results of the determination of Loading Ability indicate that for all of the Films 7a through 7d and the Films 8a through 8d, loading ability increases with thickness reaching a maximum of approximately 30 mg at a thickness of 40 mils. These results generally indicate that increasing a thickness of the Films may reduce a speed of dissolution following consumption, thus resulting in an ability to release the medicament over time.

Figure 5:
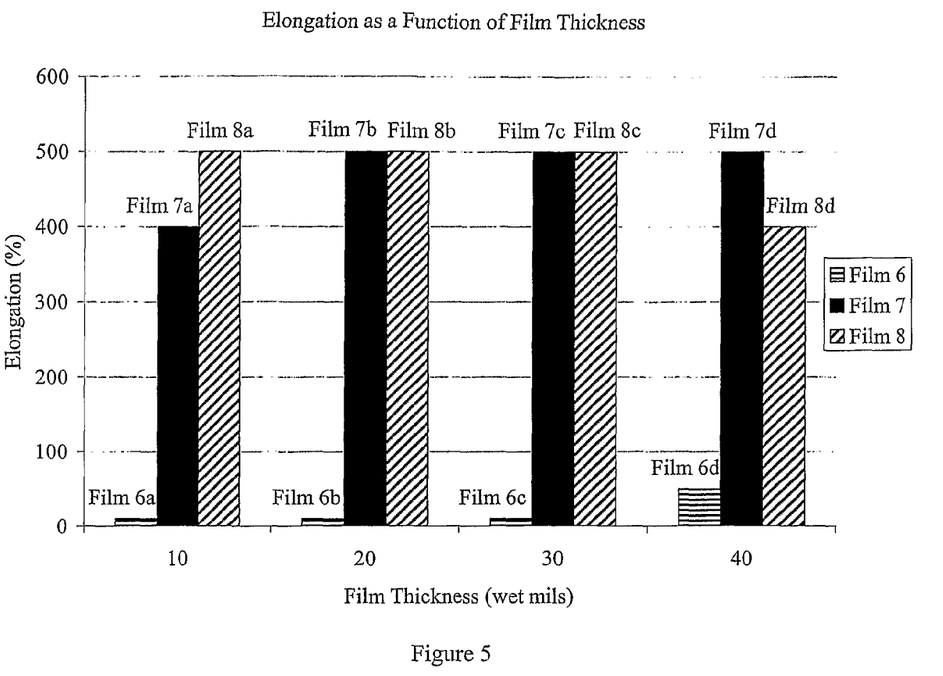
FIG. 5 is a bar graph illustrating Elongation as a Function of Film Thickness of Films 6a through 6d, 7a through 7d, and 8a through 8d.

The results of the determination of Elongation indicate that the Films 6a through 6d exhibit less ability to stretch under tension than the Films 7a through 7d and the Films 8a through 8d. These results generally indicate that an increased flexibility increases a stability of the Films. If not flexible, the Films may be brittle and exhibit tendencies to break, thereby decreasing an ability to be used commercially.

Figure 6:
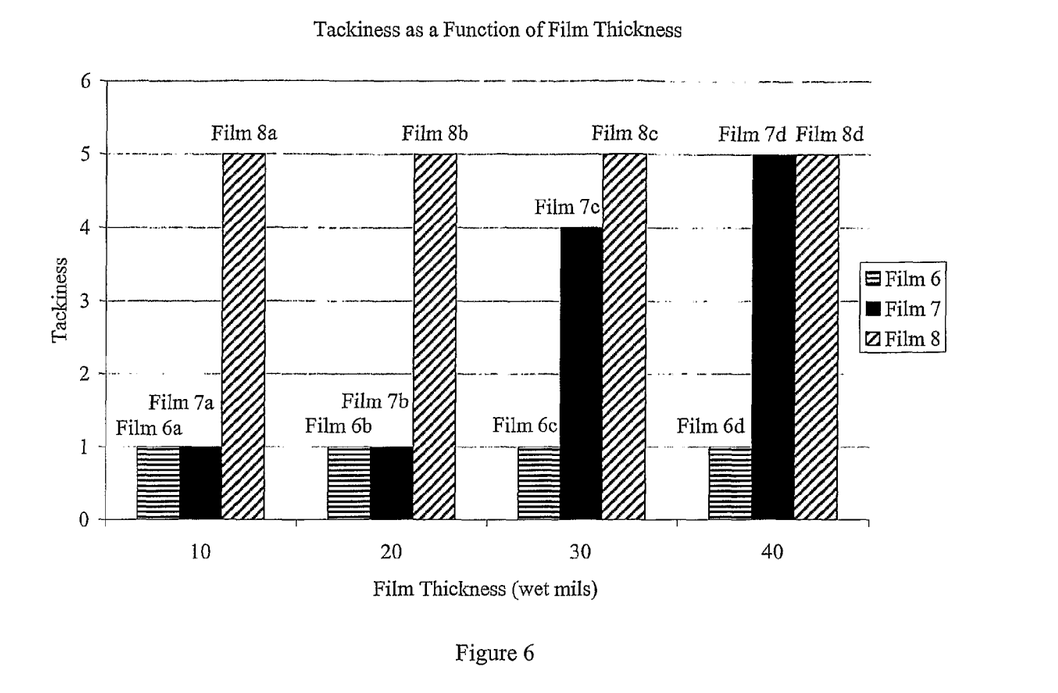
FIG. 6 is a bar graph illustrating Tackiness as a Function of Film Thickness of Films 6a through 6d, 7a through 7d, and 8a through 8d.

The results of the determination of Tackiness indicate that the Films 6a through 6d exhibit little tackiness regardless of thickness. In contrast, the Films 7a through 7d and the Films 8a through 8d exhibit increasing tackiness with increasing thickness. These results generally indicate that a decreased Tackiness of the Films allows the Films to be more readily utilized commercially as decreased Tackiness is proportional to decreased stickiness. The Films including decreased amounts of the medicament are less likely to exhibit Tackiness than those Films including increased amounts of the medicament.

Obviously, many modifications and variations of the present invention are possible in light of the above teachings. The invention may be practiced otherwise than as specifically described within the scope of the appended claims.

What is claimed is:

1. A medicament carrier composition for use in forming a single layer film having a thickness from 10 to 50 microns, said composition comprising:
   a) a medicament;
   b) a polymer component comprising a polyvinylpyrrolidone homopolymer having a weight average molecular weight of at least 700,000 g/mol;
   c) ethanol and/or water;
   d) a plasticizer that is polyethylene glycol; and
   e) an auxiliary polymer chosen from a vinylpyrrolidone-vinyl acetate copolymer, a polyethylene glycol grafted polyvinylalcohol, and combinations thereof;
   wherein said medicament carrier composition has a viscosity of from 500 to 5,000 cps at 25° C. and wherein said polymer component is present in an amount of from 10 to 15 parts by weight per 100 parts by weight of said medicament carrier composition; and
   wherein said film has a dissolution time of less than or equal to 300 seconds.

2. A medicament carrier composition as set forth in claim 1 wherein said polyvinylpyrrolidone homopolymer has a weight average molecular weight of from 700,000 to 1,000,000 g/mol.

3. A medicament carrier composition as set forth in claim 1 substantially free of cellulose.

4. A medicament carrier composition as set forth in claim 1 wherein said polymer component consists essentially of said polyvinylpyrrolidone homopolymer.

5. A medicament carrier composition as set forth in claim 1 further comprising an additive selected from the group of an anti-tacky agent, a masking agent, an antioxidant, an excipient, a sweetener, a colorant, an emulsifier, a saliva stimulating agent, a cooling agent, a stabilizing agent, a binding agent, a fragrance, and combinations thereof.

6. A medicament carrier composition as set forth in claim 1 wherein said medicament is selected from the group of pharmaceuticals, nutrients, vitamins, minerals, cosmeceuticals, cosmetics, and combinations thereof.

7. A medicament carrier composition as set forth in claim 1 wherein said medicament is selected from the group of ibuprofen, diphenhydramine hydrochloride, and combinations thereof.

8. A medicament carrier composition as set forth in claim 1 wherein said medicament comprises a vitamin.

9. A medicament carrier composition as set forth in claim 1 wherein said medicament is present in an amount of from 100 to 1000 mg per 10 grams of said composition.

10. A medicament carrier composition as set forth in claim 1 having a viscosity of from 1,500 to 3,500 centipoises at 25° C.

11. A medicament carrier composition as set forth in claim 1 wherein said composition is substantially free of cellulose, further comprises an additive selected from the group of an anti-tacky agent, a masking agent, an antioxidant, an excipient, a sweetener, a colorant, an emulsifier, a saliva stimulating agent, a cooling agent, a stabilizing agent, a binding agent, a fragrance, and combinations thereof, said medicament is selected from the group of pharmaceuticals, nutrients, vitamins, minerals, cosmeceuticals, cosmetics, and combinations thereof, and present in an amount of from 100 to 1000 mg per 10 grams of said composition, and wherein said composition has a viscosity of from 1,500 to 3,500 centipoises at 25° C.

12. A single layer film formed from said medicament carrier composition as set forth in claim 1 wherein said polyvinylpyrrolidone homopolymer is present in an amount of from 85 to 99.9 parts by weight per 100 parts by weight of said film.

13. A single layer film as set forth in claim 12 having a surface area of from 2 to 20 square centimeters.

14. An article comprising said single layer film as set forth in claim 12.

15. A method of forming a single layer film having a thickness from 10 to 50 microns from a medicament carrier composition comprising a medicament, a polymer component comprising a polyvinylpyrrolidone homopolymer having a weight average molecular weight of at least 700,000 g/mol, ethanol and/or water, a plasticizer that is polyethylene glycol, and an auxiliary polymer chosen from a vinylpyrrolidone-vinyl acetate copolymer, a polyethylene glycol grafted polyvinylalcohol, and combinations thereof, said method comprising the steps of:
   a) providing the medicament;
   b) providing the polymer component;
   c) providing the ethanol and/or water;
   d) providing the plasticizer;
   e) providing the auxiliary polymer;
   f) combining the polymer component, the medicament, the ethanol and/or water, the plasticizer, and the auxiliary polymer to form the medicament carrier composition having a viscosity of from 500 to 5,000 cps at 25° C.;
   g) drying the medicament carrier composition to form the film,
   wherein the polymer component is present in the medicament carrier composition in an amount of from 10 to 15 parts by weight per 100 parts by weight of the medicament carrier composition; and
   wherein the film has a dissolution time of less than or equal to 300 seconds.

16. A method as set forth in claim 15 wherein the step of combining is such that the film comprises from 1 to 30 mg of the medicament.

17. A method as set forth in claim 15 wherein the step of drying is further defined as drying the medicament carrier composition to form the film having a surface area of from 2 to 20 square centimeters.

18. A method as set forth in claim 15 wherein the step of drying is further defined as drying at a temperature of from 30 to 90° C. and for a time of from 10 to 30 minutes.

19. A method as set forth in claim 15 wherein the film is substantially free of cellulose.

20. A method as set forth in claim 15 wherein the step of providing the polymer component is further defined as providing a polymer component having a weight average molecular weight of from 700,000 to 1,000,000 g/mol.

21. A method as set forth in claim 15 wherein the step of providing the polymer component is further defined as providing a polymer component consisting essentially of the polyvinylpyrrolidone homopolymer having the weight average molecular weight of at least 700,000 g/mol.

22. A method as set forth in claim 15 further comprising the step of applying the medicament carrier composition onto a surface of a mold.

23. A method as set forth in claim 15 further comprising the step of applying the medicament carrier composition onto a backing layer.

* * * * *